United States Patent
Huang

(10) Patent No.: US 10,272,362 B2
(45) Date of Patent: Apr. 30, 2019

(54) METHOD OF EXTRACTING TAIWAN HYPERICUM EXTRACT, TAIWAN HYPERICUM EXTRACT, AND USE OF THE TAIWAN HYPERICUM EXTRACT

(71) Applicant: TRIDL TECHNOLOGIES INC., Tainan (TW)

(72) Inventor: Ho Shin Huang, Tainan (TW)

(73) Assignee: TRIDL TECHNOLOGIES INC., Tainan (TW)

( * ) Notice: Subject to any disclaimer, the term of this patent is extended or adjusted under 35 U.S.C. 154(b) by 0 days.

(21) Appl. No.: 15/814,182

(22) Filed: Nov. 15, 2017

(65) Prior Publication Data

US 2019/0070522 A1  Mar. 7, 2019

(30) Foreign Application Priority Data

Sep. 7, 2017  (TW) .............................. 106130589 A

(51) Int. Cl.
| | | |
|---|---|---|
| *A61K 36/00* | (2006.01) | |
| *B01D 11/02* | (2006.01) | |
| *A61K 36/38* | (2006.01) | |
| *A61K 8/96* | (2006.01) | |
| *A61Q 19/08* | (2006.01) |

(52) U.S. Cl.
CPC ............ *B01D 11/0265* (2013.01); *A61K 8/96* (2013.01); *A61K 36/38* (2013.01); *A61Q 19/08* (2013.01); *A61K 2236/15* (2013.01); *A61K 2236/17* (2013.01); *A61K 2236/33* (2013.01); *A61K 2236/51* (2013.01)

(58) Field of Classification Search
None
See application file for complete search history.

(56) References Cited

FOREIGN PATENT DOCUMENTS

CN          101264122 A  *  9/2008

OTHER PUBLICATIONS

Karim Hosni, Kamel Msaâda, Mouna Ben Taârit, Mohammed Hammami, Brahim Marzouk; Bioactive components of three *Hypericum* species from Tunisia: A comparative study; Nov. 2, 2009 ; Industrial Crops and Products, vol. 31, Issue 1, Jan. 2010, pp. 158-163.

Hoe-Yune Jung, Jae-Cheon Shin, Seon-Min Park, Na-Ri Kim, Wonjung Kwak, Bo-Hwa Choi; Pinus densiflora extract protects human skin fibroblasts against UVB-induced photoaging by inhibiting the expression of MMPs and increasing type I procollagen expression; Aug. 29, 2014; Toxicology Reports, vol. 1, 2014, pp. 658-666.

Subramanian Umadevi, Venkatachalam Gopi, Elangovan Vellaichamy; Inhibitory Effect of Gallic Acid on Advanced Glycation End Products Induced Up-Regulation of Inflammatory Cytokines and Matrix Proteins in H9C2 (2-1) Cells; Sep. 24, 2013, Cardiovascular Toxicology, vol. 13, Issue 4, pp. 396-405.

Shen-Shien Chang and Yi-Rung Chen, Comparison and Analysis of Antioxidant Capacity of Hypericum, Bull. Hualien DARES 33:21-32(2013), Taiwan.

* cited by examiner

*Primary Examiner* — Qiuwen Mi
(74) *Attorney, Agent, or Firm* — Ming Chow; Sinorica, LLC

(57) ABSTRACT

Provided is a method for extracting a Taiwan *hypericum* extract, including the steps of: preparing a *Hypericum formosanum* Maxim plant tissue, and drying and crushing the *Hypericum formosanum* Maxim plant tissue to obtain a Taiwan *hypericum* powder; soaking the Taiwan *hypericum* powder in an organic solvent; ultrasonicating the Taiwan *hypericum* powder soaked in the organic solvent, obtaining a rough extract; and filtering the rough extract to obtain the Taiwan *hypericum* extract. Provided is a Taiwan *hypericum* extract obtained by the method described above. Provided is a method for anti-glycation and anti-photoaging including a step of administering to a subject a therapeutically effective amount of the Taiwan *hypericum* extract described above. Provided is a cosmetic care product which comprises the Taiwan *hypericum* extract described above and a dermatologically acceptable adjuvant.

1 Claim, 8 Drawing Sheets

METHOD OF EXTRACTING TAIWAN HYPERICUM EXTRACT, TAIWAN HYPERICUM EXTRACT, AND USE OF THE TAIWAN HYPERICUM EXTRACT

CROSS-REFERENCE TO RELATED PATENT APPLICATION

This application claims priority under 35 U.S.C. § 119(a) to Taiwan Patent Application No. 106130589, filed on Sep. 7, 2017, the content of which is hereby incorporated by reference in its entirety.

BACKGROUND OF THE INVENTION

1. Field of the Invention

The present invention relates to a method, especially a method for extracting a Taiwan *hypericum* extract. The present invention also relates to a Taiwan *hypericum* extract obtained by the method. The present invention further relates to a method for anti-glycation and anti-wrinkle with a composition comprising the Taiwan *hypericum* extract. The present invention also relates to a cosmetic product comprising the Taiwan *hypericum* extract and a dermatologically acceptable adjuvant.

2. Description of the Prior Arts

Nowadays people pay much attention to their appearance and skin care. Meanwhile, climate anomaly and ozone depletion have increased demands for sunscreen and skin aging-related products, and thus the market for cosmetic products has been expanding year by year. The artificial chemical products have been replaced by natural ingredients in the cosmetic products, and thus the application of natural beauty products extracted from plants has been widely valued; especially the application of plant extracts to cosmetic products has become a global trend.

Glycation is a major cause of aging and disease. The essence of glycation is the Maillard reaction, which is a non-enzymatic reaction between the aldehyde (ketone) of sugar and the amine of the substances such as protein, peptide, amino acid, phospholipids, nucleic acids or derivatives thereof. Advanced glycation end products (AGEs) are generated in the late stages of Maillard reaction in foods and biological systems. With excessive intake of carbohydrate foods, the excess sugar and protein will generate AGEs, causing aging of the skin and the body cells. In recent years, it has been found that there are many natural ingredients, such as curcumin and rosemary, and flavonoids such as rutin, which can effectively reduce the formation of AGEs and protect the organism from the damage caused by glycation.

Many studies have shown that matrix metalloproteinases (MMPs) are enzymes associated with skin aging. The abnormal secretion of MMPs in the skin cells will break down the connective tissue and cause wrinkles. In normal, healthy or resting tissue, MMPs are hardly present or remain in a minim state, while when the cells or tissues are under repair or remodeling, various types of MMPs will be secreted in large quantity.

It is difficult to avoid the intrinsic aging of skin, but it is possible to prevent, or even remedy the extrinsic aging. Therefore, the present invention provides a plant component with the effect of anti-glycation and MMPs inhibition to delay, and even avoid skin damage and smooth skin wrinkles or relieve other aging phenomena.

The *Hypericum* genus plants are widely distributed in Europe, Asia, and North America, and are applied as medicinal herbs in many parts of the world. Among them, the Taiwan *Hypericum* is a *hypericum* genus of the genus *Hypericum chrysanthemum*, which is known as *Hypericum formosanum* Maxim, belonging to Taiwan endemic species. It is yet still unseen in the prior arts to use the Taiwan *Hypericum* in anti-glycation and anti-aging or other applications.

SUMMARY OF THE INVENTION

Accordingly, the object of the present invention is to provide a method for extracting a Taiwan *hypericum* extract, which can prevent and delay skin aging by anti-glycation and anti-photoaging.

To achieve the above object, the present invention provides a method of extracting a Taiwan *hypericum* extract, comprising the steps of:

(1) preparing a *Hypericum formosanum* Maxim plant tissue, and drying and crushing the *Hypericum formosanum* Maxim plant tissue to obtain a Taiwan *hypericum* powder;

(2) soaking the Taiwan *hypericum* powder in an organic solvent, wherein the volume ratio of the Taiwan *hypericum* powder to the organic solvent is between 1:5 and 1:15;

(3) ultrasonicating the Taiwan *hypericum* powder in the organic solvent to obtain a rough extract;

(4) filtering the rough extract to obtain the Taiwan *hypericum* extract.

Preferably, during the step (1), the *Hypericum formosanum* Maxim plant tissue is whole-plant *Hypericum formosanum* Maxim.

Preferably, in the step (2), the organic solvent is ethanol, methanol or ethyl acetate.

More preferably, the concentration of ethanol is between 50% and 80%. More preferably, the concentration of ethanol is 65%.

Preferably, during the step (3), the ultrasonication is performed at a temperature between 55° C. and 80° C. with a frequency between 25 Hz and 40 Hz for an extraction time between 30 minutes to 60 minutes.

Preferably, the step (4) further comprises a concentration step after the filtering step, which uses vacuum concentration or lyophilization to remove the organic solvent contained in the Taiwan *hypericum* extract. More preferably, the concentration step uses the vacuum concentration to remove the organic solvent, concentrated and dried.

The present invention further provides a Taiwan *hypericum* extract obtained by the method described above. The Taiwan *hypericum* extract can prevent and delay skin aging by anti-glycation and anti-photoaging.

Preferably, the Taiwan *hypericum* extract comprises at least one flavonoid active compound.

More preferably, the at least one flavonoid active compound includes, but is not limited to, hyperoside, astilbin, quercitrin, and quercetin.

The present invention further provides a cosmetic care product comprising the Taiwan *hypericum* extract obtained by the method described above and a dermatologically acceptable adjuvant.

The dermatologically acceptable adjuvant in accordance with the present invention includes, but is not limited to, aqueous solution, water-alcohol solution, oily solution, oil-in-water emulsion, water-in-oil emulsion, composite emulsion, mask, aqueous gel, oily gel, aerosol, cream, ointment, milk, lotion, serum, paste, mousse, foam, dispersion and any other similar or applicable adjuvant of the present invention.

The advantages of the present invention are that the method can obtain the Taiwan *hypericum* extract containing high content of flavonoid active compounds, and the obtained Taiwan *hypericum* extract has the effects of anti-glycation, anti-aging, anti-wrinkle, and delayed skin aging.

Other objectives, advantages and novel features of the invention will become more apparent from the following detailed description when taken in conjunction with the accompanying drawings.

DETAILED DESCRIPTION OF THE PREFERRED EMBODIMENTS

Preparation Example 1: Preparation of the Taiwan *Hypericum* Extract

The tissues of *Hypericum formosanum* Maxim including the leaves, stem, and root were harvested. The samples were washed with water and dried at a temperature between 5° C. to 35° C. After that, the dried samples were ground by an electronic blender to obtain a Taiwan *hypericum* powder. The Taiwan *hypericum* powder was mixed with ethanol at a volume ratio of 1:10, and then ultrasonicated at a temperature between 55° C. and 80° C. with a frequency between 25 Hz and 40 Hz for an extraction time between 30 minutes to 60 minutes, so as to obtain a rough extract. After extraction, the rough extract was instantly filtered through the filter paper under reduced pressure, and the Taiwan *hypericum* extract was obtained.

Preparation Example 2: Cell Culture of Human Keratinocytes (HaCat)

HaCaT cells were cultured in Dulbecco's modified Eagle's medium (DMEM; Gibco Life Technologies, Grand Island, N.Y., USA) supplemented with 10% fetal bovine serum (FBS; Thermo Fisher Scientific, Waltham, Mass., USA) and 1% penicillin-streptomycin. HaCaT cells were maintained in a humidified atmosphere with 5% $CO_2$ at 37° C. When HaCaT cells reached 90% confluency, the medium was removed from the flask and the HaCaT cells were rinsed twice with phosphate buffered-saline (PBS). 1 mL to 2 mL trypsin-EDTA was added and left until all HaCaT cells had rounded up and begun to detach for 5 minutes at 37° C. in 5% $CO_2$ incubator, followed by centrifuging the HaCaT cells at 1,250 rpm for 5 minutes and pouring off supernatant and resuspending with fresh medium, and finally seeding in a new flask. Each flask was added with about 12 mL medium, and the medium was replaced at intervals of about 1 day to 2 days.

Preparation Example 3: Cell Culture of Primary Normal Human Dermal Fibroblasts (NHDFs)

2 $cm^2$ to 4 $cm^2$ normal human skin was obtained and soaked in DMEM with dispase II at 37° C. for 2 hours to isolate the epithelial tissue and the dermal tissue, and the dermal tissue was then transferred and soaked into 0.1% collagenase I for 24 hours, followed by adding DMEM and centrifuging at 1,000 rpm for 5 minutes, pouring off supernatant and resuspending with DMEM supplemented with 20% fetal calf serum (FCS), and then seeding in 10 cm cell culture dishes in a humidified atmosphere with 5% $CO_2$ at 37° C.

Example 1 Bioactive Compounds Identification of Taiwan *Hypericum* Extract

The Taiwan *hypericum* extract which was obtained in preparation example 1 was analyzed by high performance liquid chromatography (HPLC).

The analytical conditions of HPLC were as follows: column: T3 (100 mm×3 mm); mobile phase A: water; mobile phase B: methanol (containing 1% formic acid); gradient setting: 0 minute to 5 minutes as 85% A, 5 minutes to 10 minutes as 30% A, 10 minutes to 15 minutes as 0% A, and 15 minutes to 20 minutes as 85% A; flow rate: 0.4 mL/min; and detection wavelength: 200 nm to 400 nm.

Figure 1:
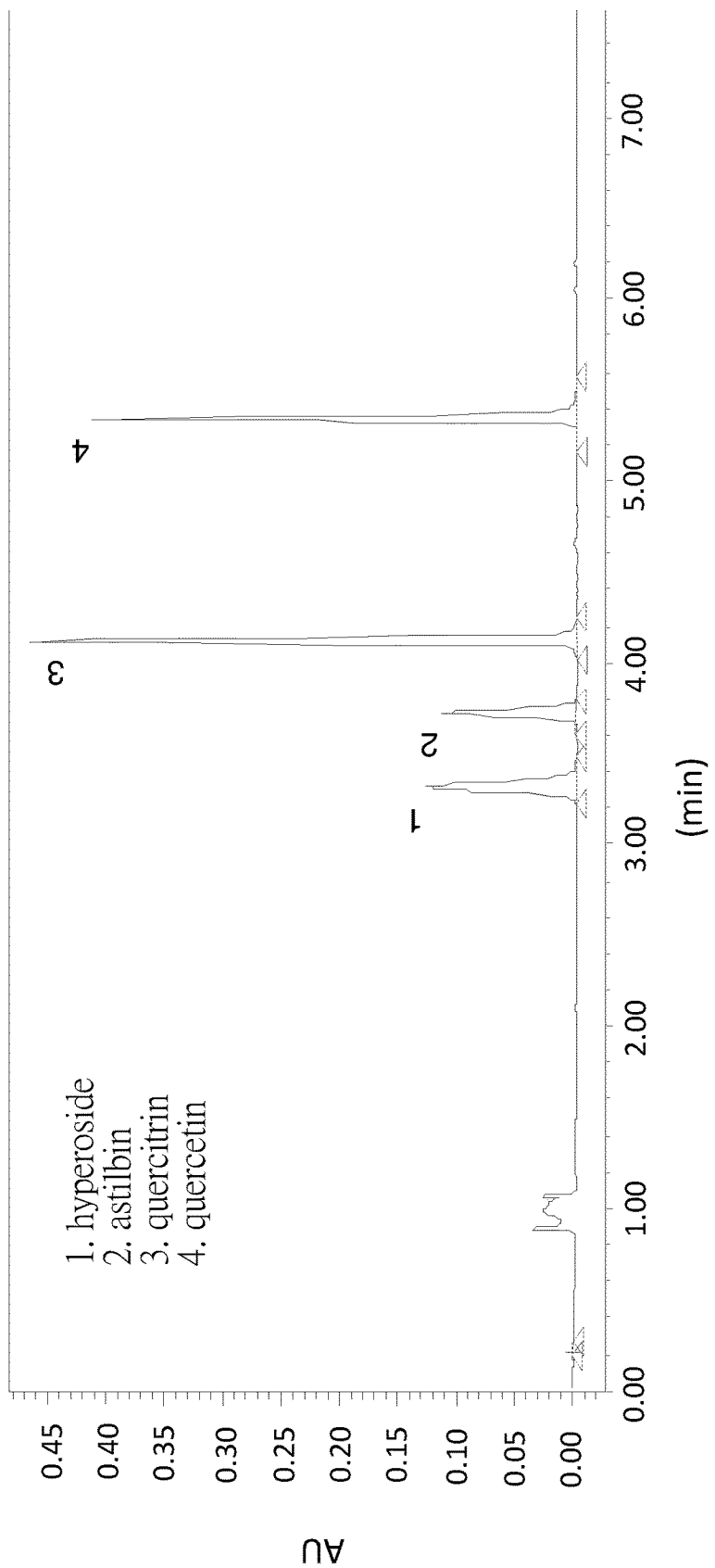
FIG. 1 shows the results of HPLC analysis of the Taiwan *hypericum* extract.

Referring to FIG. 1, the Taiwan *hypericum* extract was rich in flavonoids, compared with the standard. In addition, the main flavonoids in the Taiwan *hypericum* extract include hyperoside, astilbin, quercitrin, and quercetin, and the contents of the compounds of the Taiwan *hypericum* extract (prepared from Preparation Example 1) are as shown in Table 1 below.

TABLE 1

Content of flavonoids in the Taiwan hypericum extract.

| Compound | The contents of the compounds of Taiwan hypericum extract (mg/g) |
|---|---|
| Hyperoside | 2.27 ± 0.05 |
| Astilbin | 4.33 ± 0.05 |
| Quercitrin | 8.56 ± 0.05 |
| Quercetin | 1.53 ± 0.05 |

Example 2 Total Flavonoid Content (TFC) of the Taiwan *Hypericum* Extract

It is known from Example 1 that the Taiwan *hypericum* extract has a variety of flavonoid active compounds. In this example, the effect of the ethanol concentration, the ultrasonic extraction temperature and the extraction time on the TFC of the Taiwan *hypericum* extract was tested using the total flavonoid content assay. TFC was determined based on the Kim's method with some modifications. 1 mL of diluted Taiwan *hypericum* extract solution (1 mg/mL) was mixed with 0.3 mL of 5% $NaNO_2$ and 4 mL of deionized water and left standing for 5 minutes. And then 0.3 mL of 10% $AlCl_3.6H_2O$ was added to the mixture for 6 minutes followed by adding 2 mL of 1 M NaOH and the solution was immediately diluted to 10 mL with deionized water. The absorbance of the solution was measured at 570 nm. Results of total flavonoid content were expressed as g of catechin equivalents (CE) on dry weight of the Taiwan *hypericum* extract (mg CE/g DW). All experiments were performed in triplicate. The test results are shown in FIGS. 2A to 2C.

Figure 2A:
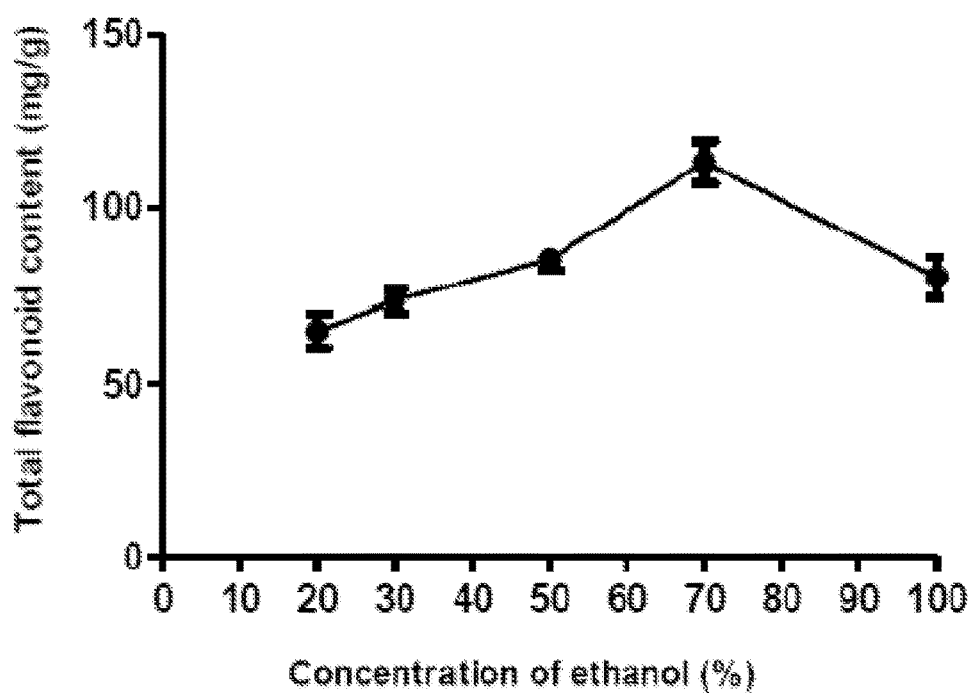
FIG. 2A shows the line chart of extraction time on the total flavonoid content of the Taiwan *hypericum* extract.
Figure 2B:
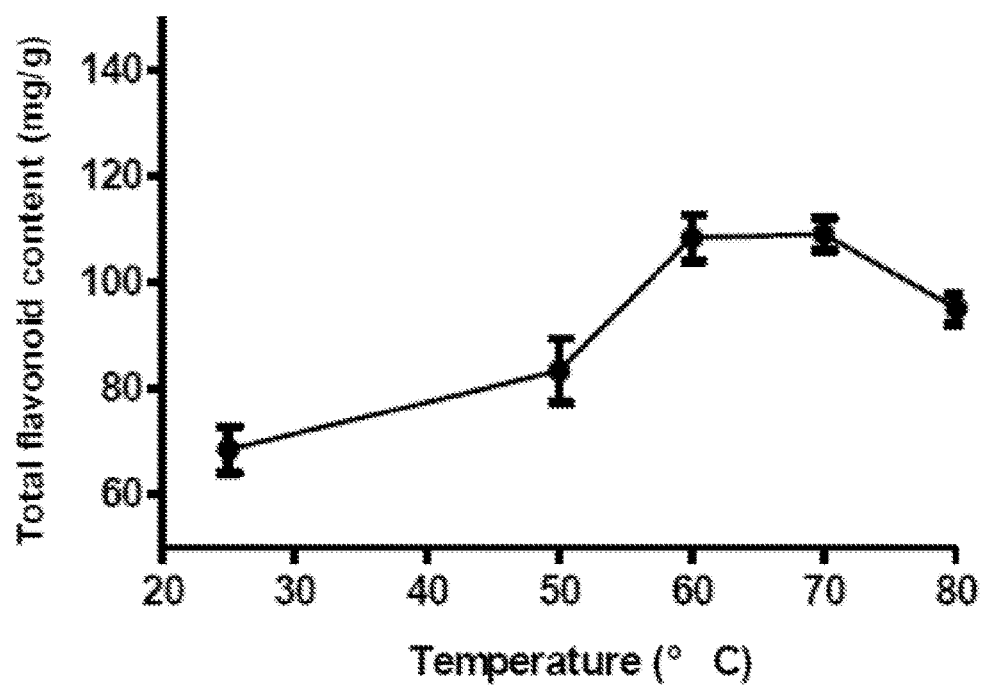
FIG. 2B shows the line chart of extraction temperature on the total flavonoid content of the Taiwan *hypericum* extract.
Figure 2C:
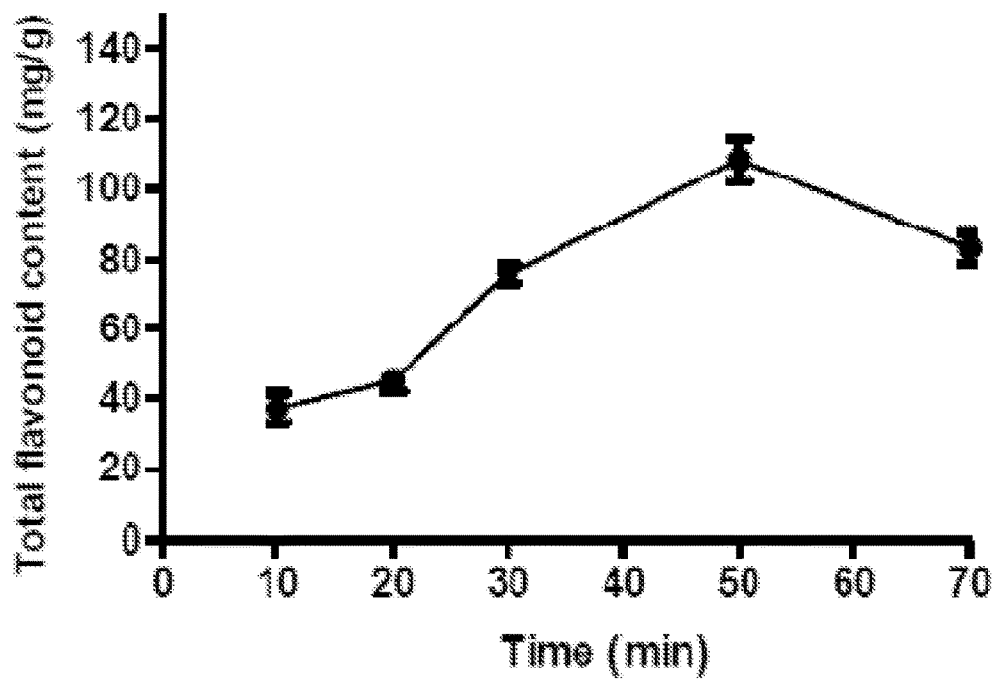
FIG. 2C shows the line chart of ethanol concentration on the total flavonoid content of the Taiwan *hypericum* extract.

Referring to FIG. 2A, the TFC of the Taiwan *hypericum* extract was more than 100 mg/g when the ethanol concentration was between 65% and 80%. Referring to FIG. 2B, the TFC of the Taiwan *hypericum* extract was more than 100 mg/g when the extraction time was between 45 minutes and 55 minutes. Referring to FIG. 2C, the TFC of the Taiwan *hypericum* extract was more than 100 mg/g when the extraction temperature was between 58° C. and 78° C.

Example 3 Optimization of Ultrasonication Step of the Taiwan *Hypericum* Extraction To obtain the highest content of flavonoid active compounds of the Taiwan *hypericum* extract, the box-Behnken design (BBD) response surface methodology (RSM) was used in this example. The three-factor third-order experimental scheme was used to extract the TFC as the reaction index. The optimal extraction method was obtained by mathematical calculation and statistical analysis to reduce the experimental cost and the number of times, and effectively extract the highest content of flavonoid active compounds of the Taiwan *hypericum* extract. Thus, the Design Expert Version 8.0 software designed the extraction variables including the ethanol concentration as X1, extraction time as X2 and extraction temperature as X3; experimental factor coding and class design were shown in Table 2.

TABLE 2

Independent variables and their coded and actual values used for optimization.

| Independent variable | Symbol | Coded level −1 | 0 | 1 |
|---|---|---|---|---|
| Concentration of ethanol | X1 | 20 | 60 | 100 |
| Extraction time | X2 | 10 | 40 | 70 |
| Extraction temperature | X3 | 25 | 52.5 | 80 |

The process variables were coded according to the following equation:

$$x=(X_i-X_0)/\Delta X,$$

wherein x is the coded value, Xi is the actual value of the variable, X0 is the actual value of the variable at the center point, and ΔX is the incremental change in the value. The experimental data were fitted to the second-order polynomial equation given below:

$$Y=\beta_o+\Sigma\beta_i X_i+\Sigma\beta_{ii}X_i^2+\Sigma\beta_{ij}X_iX_j$$

wherein Y is the predicted response (TFC) and β0, βi, βii, and βij are the regression coefficients for the intercept, linear, quadratic, and interaction terms, respectively. Xi and Xj are independent variables. Comparisons of the means were performed using one-way analysis of variance (ANOVA) followed by Tukey's post-hoc test (p<0.05). The extraction conditions were optimized for the maximum yield of TFC with high antioxidant activities based on the regression analysis and the 3D surface plots of the independent variables. The responses were determined under the recommended conditions for the extraction. Finally, the predicted values were compared with the experimental value to determine the validity of the model. The model established from the regression equation can be used to replace the experimental values to explain the observed response results. The regression equation used was $$Y=103.91A+5.44B+1.82C+3.75AB-0.1AC-2.5BC-24.63A^2-13.06B^2-6.04C^2$$

The optimal extraction method was obtained by mathematical calculation and statistical analysis to reduce the experimental cost and the number of times and effectively extract the highest content of flavonoid active compound of the extract.

Following the parameter optimization based on the constructed mathematical model, the experimental conditions obtained were: ethanol concentration: 65%; extraction time: 47 minutes; and extraction temperature: 65° C. Under the optimal conditions, the predicted extraction rate of total flavonoids was 107 mg/g (data not shown).

Example 4 Anti-Glycation Test

AGEs would be produced during glycation of albumin with glucose. The higher the content of AGEs, the higher the fluorescence intensity. The concentrations of 0 µg/mL (as the control group), 100 µg/mL, 200 µg/mL and 400 µg/mL of the Taiwan *hypericum* extract prepared from Preparation Example 1 were respectively prepared with 0.1 M pH7.4 PBS supplemented with 500 mM glucose, 20 mg/mL of bovine serum albumin (BSA), and 0.02% sodium azide.

The incubation was at 37° C. and under dark conditions for glycation. The experiment lasted for 5 weeks and was sampled once every week, respectively as the 0, 1st, 2nd, 3rd, 4th and 5th weeks. The fluorescence intensity was activated at 370 nm and the fluorescence intensity of AGEs was measured at 440 nm. The results are shown in FIG. 3.

Figure 3:
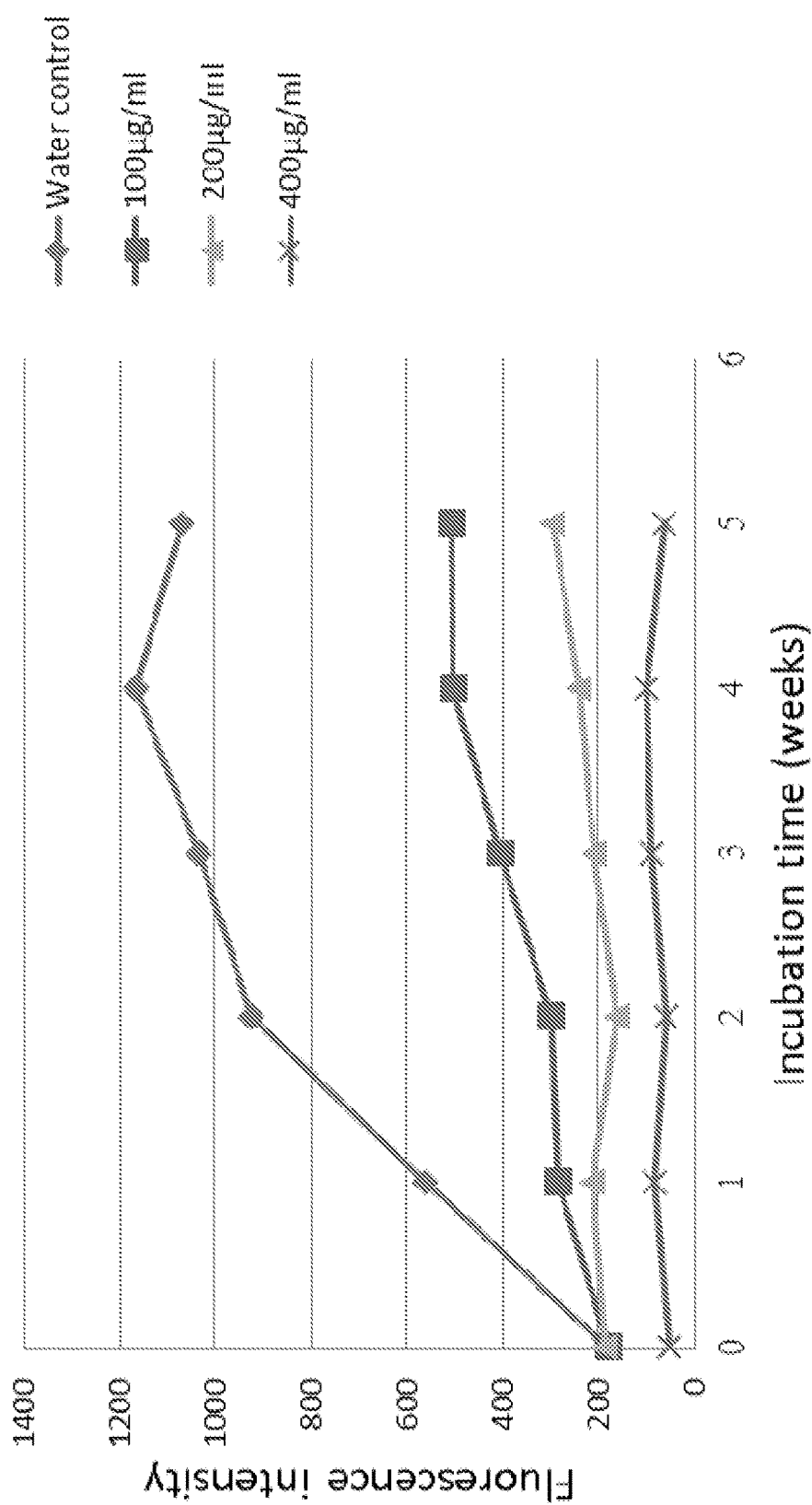
FIG. 3 shows the result of the anti-glycation test of the Taiwan *hypericum* extract.

Referring to FIG. 3, compared with the control group, the fluorescence intensities of the groups containing the Taiwan *hypericum* extract were significantly reduced. With the reduction of the AGEs content, the fluorescence intensity (AGEs content) was dependently decreased with the increase of the concentration of the Taiwan *hypericum* extract. These results show that the Taiwan *hypericum* extract has the effect of anti-glycation.

HaCaT cells were seeded in culture dishes and added with 100 µg/mL advanced glycation end product-modified bovine albumin (AGE-BSA) for glycation for 24 hours, rinsed with serum free medium twice to remove the AGE-BSA, and then respectively added with 0 µg/mL (as the control group) and the 200 µg/mL of the Taiwan *hypericum* extract (dissolved in DMSO, DMSO final concentration is 0.5%) prepared from Preparation Example 1, wherein one group of HaCaT cells not treated with AGE-BSA nor the Taiwan *hypericum* extract was as a negative control group. After the experiment was completed, the cells were collected to extract the cell RNA, and the gene expression level of the matrix metalloproteinase-1 (MMP-1) was measured by Real-time PCR. The detailed experimental steps are within the general knowledge of the art to which this invention pertains and are not intended to be a technical feature of the present invention, and are therefore omitted here.

Figure 4:
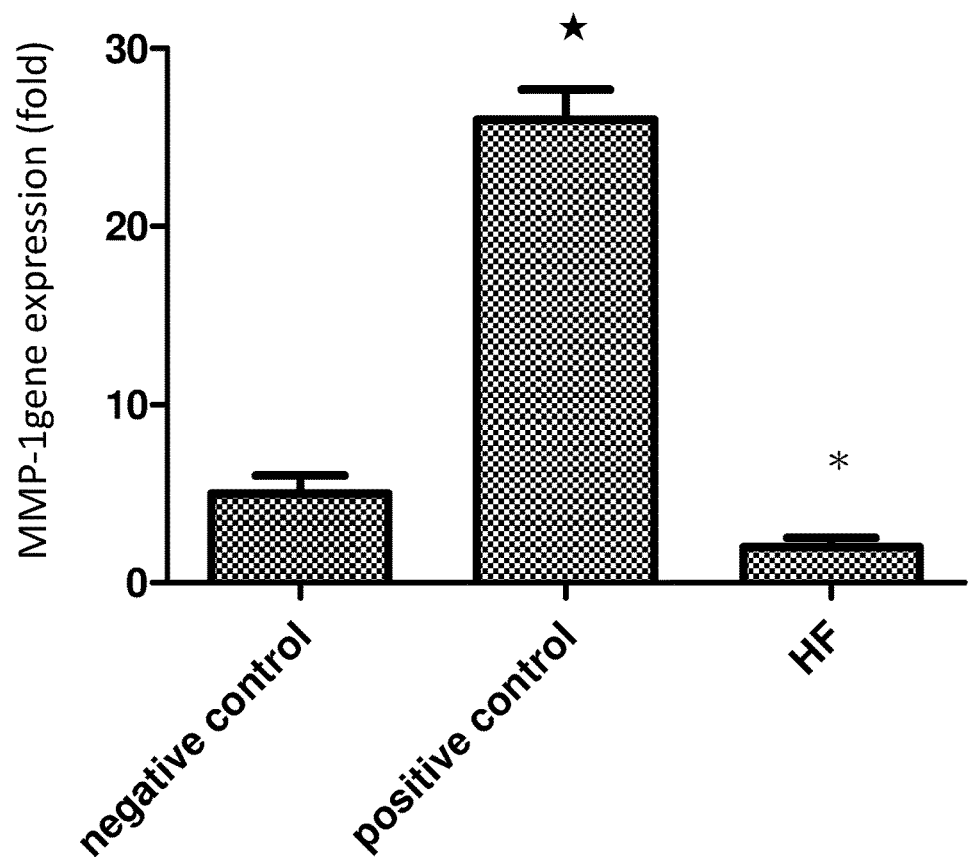
FIG. 4 shows the effect of the Taiwan *hypericum* extract on MMP-1 expression in glycation, ★ for a statistically significant difference from the negative control group ($p<0.05$), and * for a statistically significant difference from the positive control group ($p<0.05$)

According to the results shown in FIG. 4, it was observed that, after 24 hours of treatment with AGE-BSA, the gene expression of MMP-1 in the positive control group was 5.2 times thereof in the negative control group, that is, AGE-BSA stimulates the MMP-1 gene expression. After treating the HaCaT cells with 200 μg/mL of the Taiwan *hypericum* extract, the gene expression of MMP-1 was significantly decreased by 92% compared with the control group. The results showed that the Taiwan *hypericum* extract had significant inhibition of MMP-1 gene expression.

Example 5 Anti-Photoaging Test

NHDFs were seeded in 6 cm culture dish at $2\times10^5$ cells/dish and incubated for 24 hours. Cells were pretreated with the indicated doses (0 μg/mL, as control group, and 200 μg/mL) of the Taiwan *hypericum* extract prepared from Preparation Example 1 for 6 hours, and then the medium was washed with PBS, followed by UVB (5 mJ/cm$^2$) irradiation without the culture dish lid for 24 hours (one of the control groups was not treated with UVB irradiation as a negative control, while the other control group was treated with UVB irradiation as a positive control). After the irradiation, PBS was immediately replaced with fresh growth medium containing the indicated doses of the Taiwan *hypericum* extract and the cells were incubated for 24 hours. After the experiment was completed, the cells were collected and the cell RNA was extracted, and the gene expression level of MMP-1 and MMP-3 was measured by Real-time PCR. The detailed experimental steps are within the general knowledge of the art to which this invention pertains and are not intended to be a technical feature of the present invention, and are therefore omitted here.

Figure 5:
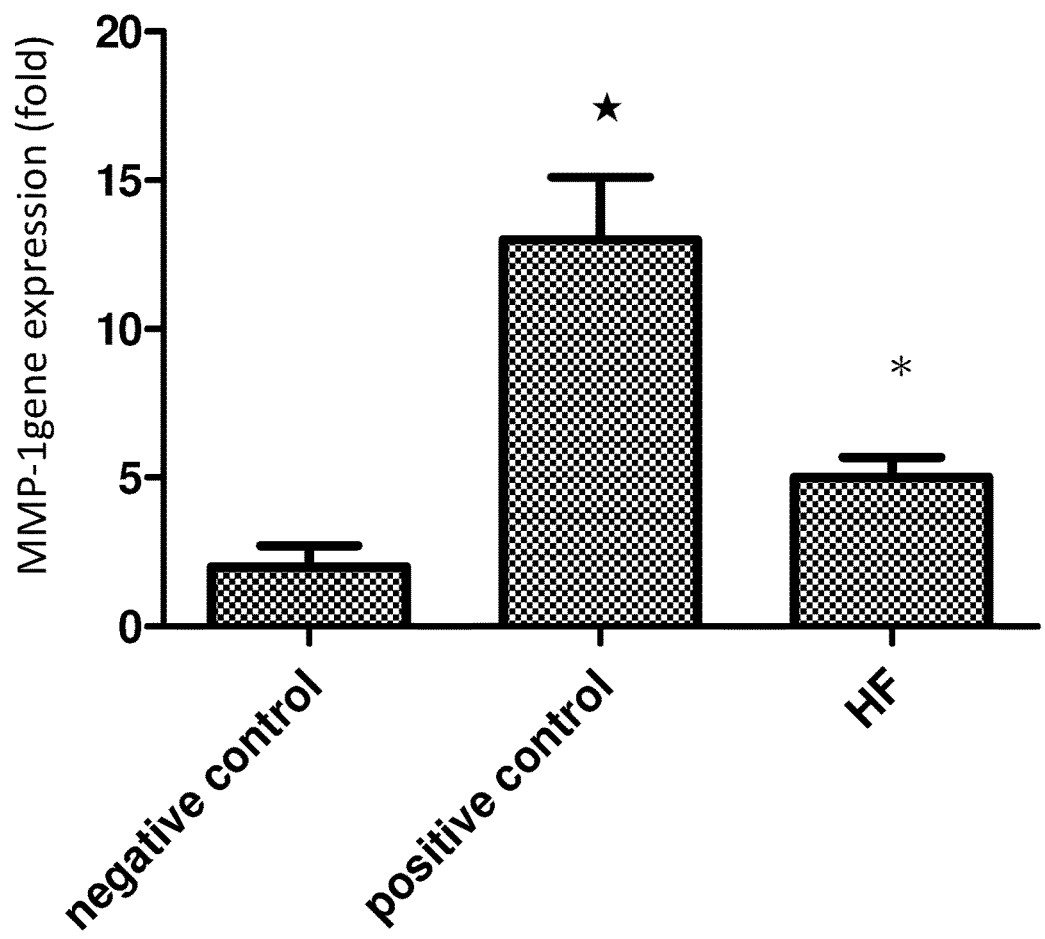
FIG. 5 shows the effect of the Taiwan *hypericum* extract on MMP-1 expression in UVB irradiation, ★ for a statistically significant difference from the negative control group ($p<0.05$), and * for a statistically significant difference from the positive control group ($p<0.05$)
Figure 6:
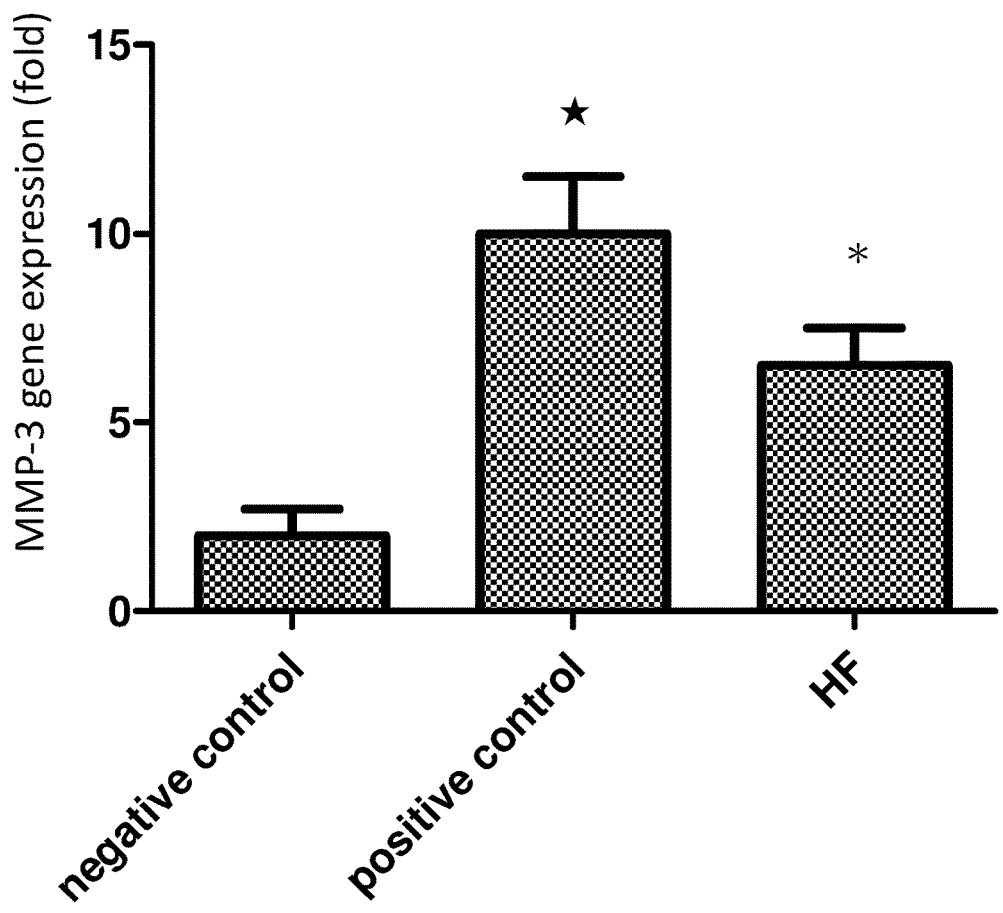
FIG. 6 shows the effect of the Taiwan *hypericum* extract on MMP-3 expression in UVB irradiation, ★ for a statistically significant difference from the negative control group ($p<0.05$), and * for a statistically significant difference from the positive control group ($p<0.05$).

According to the results shown in FIG. 5, it was observed that after 24 hours of UVB irradiation, the gene expression of MMP-1 in the positive control group was 6.5 times thereof in the negative control group, that is, UVB stimulates the MMP-1 gene expression. After treating the NHDFs with 200 μg/mL of the Taiwan *hypericum* extract, the gene expression of MMP-1 was significantly decreased by 60% compared with the positive control group, close to the level of the MMP-1 gene expression in the negative control group. According to the results shown in FIG. 6, after 24 hours of UVB irradiation, the gene expression of MMP-3 in the positive control group was 5 times thereof in the negative control group, and after treating the NHDFs with 200 μg/mL of the Taiwan *hypericum* extract, the gene expression of MMP-3 was significantly decreased by 65% compared with the positive control group.

Because the excessive secretion of MMP-1 and MMP-3 will cause the skin collagen aging and wrinkles, these results prove that the Taiwan *hypericum* extract can inhibit the expression of MMP-1 and MMP-3, and thus achieve the effect of anti-aging and anti-wrinkle by anti-glycation and anti-photoaging.

Even though numerous characteristics and advantages of the present invention have been set forth in the foregoing description, together with details of the structure and features of the invention, the disclosure is illustrative only. Changes may be made in the details, especially in matters of shape, size, and arrangement of parts within the principles of the invention to the full extent indicated by the broad general meaning of the terms in which the appended claims are expressed.

What is claimed is:

1. A method for anti-glycation and anti-photoaging, comprising a step of administering to a subject in need thereof a therapeutically effective amount of Taiwan *hypericum* extract; said extract is obtained by the steps of:
   (1) preparing a *Hypericum formosanum* Maxim plant, and drying and crushing the *Hypericum formosanum* Maxim plant to obtain a Taiwan *hypericum* powder;
   (2) soaking the Taiwan *hypericum* powder in an organic solvent, wherein the volume ratio of the Taiwan *hypericum* powder to the organic solvent is between 1:5 and 1:15;
   (3) ultrasonicating the Taiwan *hypericum* powder in the organic solvent to obtain a crude extract; and
   (4) filtering the crude extract to obtain the Taiwan *hypericum* extract.

* * * * *